United States Patent [19]
Roberge et al.

[11] Patent Number: 5,894,085
[45] Date of Patent: Apr. 13, 1999

[54] DEVICE FOR DETERMINING THE PURITY OF A METAL ALLOY

[75] Inventors: Jean-Luc Roberge, Villiers St Frederic; Michel Richard, Paris, both of France

[73] Assignee: Centre Technique des Industries de la Fonderie, France

[21] Appl. No.: 08/875,565

[22] PCT Filed: Jan. 25, 1996

[86] PCT No.: PCT/FR96/00125

§ 371 Date: Jul. 25, 1997

§ 102(e) Date: Jul. 25, 1997

[87] PCT Pub. No.: WO96/23222

PCT Pub. Date: Aug. 1, 1996

[30] Foreign Application Priority Data

Jan. 26, 1995 [FR] France ........................ 95 00877

[51] Int. Cl.[6] .................... G01N 33/20; C22B 9/02
[52] U.S. Cl. .................... 73/61.73; 73/61.41; 266/236; 75/407
[58] Field of Search .................... 73/53.01, 61.41, 73/61.71, 61.72, 61.73; 266/236; 75/407, 412; 210/85, 86

[56] References Cited

U.S. PATENT DOCUMENTS 5,095,740  3/1992  Hodgson et al. .

FOREIGN PATENT DOCUMENTS 0057965  8/1982  European Pat. Off. .
2439941  3/1976  Germany .
2848005  6/1979  Germany .
59-202063  11/1984  Japan .
4-298987  10/1992  Japan .
97/18456  5/1997  WIPO .

OTHER PUBLICATIONS

Lessiter et al. To Pour or not to Pour: The Dilemma of Assessing Your Aluminum Melt's Cleanliness, Modern Casting, pp. 45–48, Feb. 1996.

S. Ali, et al., "Physical Refining of Steel Melts by Filtration", Metallurgical Transactions/B: Process Metallurgy, vol. 16B, Nos. 1–4, Dec. 1985, pp. 725–742.

*Primary Examiner*—Michael Brock
*Attorney, Agent, or Firm*—Ostrolenk, Faber, Gerb & Soffen, LLP

[57] ABSTRACT

The invention relates to apparatus for determining the purity of a metal alloy, and in particular an aluminum alloy. The apparatus comprises a shell (10) defining a receptacle (14) of generally tapering shape about a vertical axis having a bottom end defining an orifice (18) of small dimensions, a filter (20) completely closing the orifice, means a heater for initially raising the shell to a first predetermined temperature, an orifice putting a predetermined quantity of alloy to be tested into the receptacle, the quantity of alloy being initially at a second predetermined temperature, whereby the alloy flows under gravity through the filter until the filter becomes clogged with the impurities in the alloy, and means a pan for collecting and measuring the volume of alloy that passes through the filter prior to the filter becoming clogged by the impurities contained in the alloy.

14 Claims, 4 Drawing Sheets

FIG_2

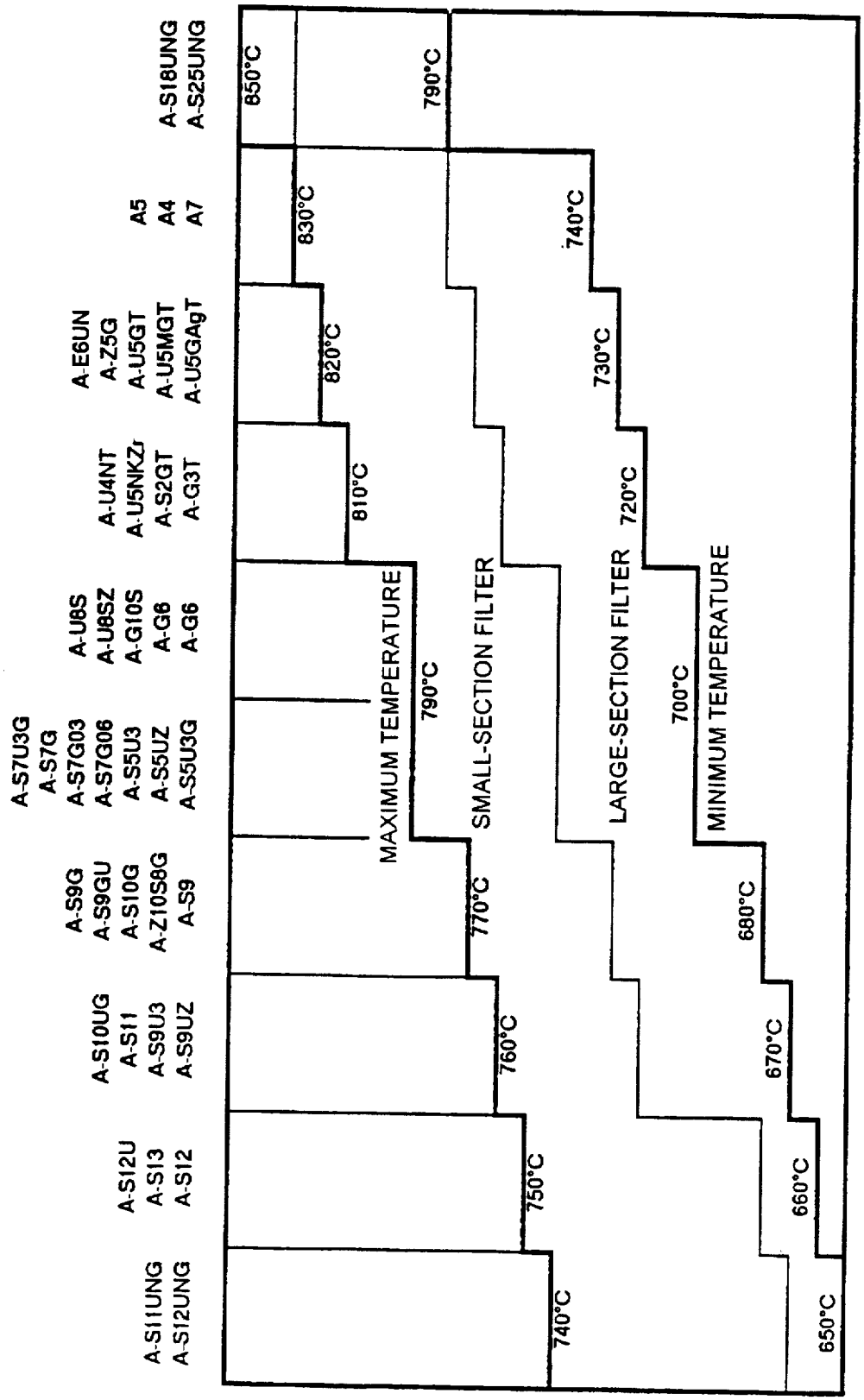
FIG._5

DEVICE FOR DETERMINING THE PURITY OF A METAL ALLOY

BACKGROUND OF THE INVENTION

The present invention relates to a method and to apparatus for determining the purity of a metal alloy.

More precisely, the invention relates to determining whether the concentration of impurities in a metal alloy, and in particular the concentration of oxides that result from making the alloy is unacceptable, acceptable, or very low so as to be able to determine whether the alloy in question is usable or not. This problem arises in particular, but not exclusively, with aluminum alloys.

These impurities that result from making the alloy, in particular an aluminum alloy, may consist essentially in oxides. Nevertheless, it is also possible to find salts, carbides, nitrides, borides, and sludge in the form of particles or of a kind of skin that forms on the alloy.

It will be understood that it is necessary, or at least desirable, once an alloy has been made, to ensure that it does not include too high a content of impurities, which could make use of the alloy difficult or impossible for making certain types of part subjected to high mechanical stresses.

Various methods have been used for determining impurity content. These various methods comprise: spectroscopic emission; various types of chemical analysis, e.g. gas chromatography; another type of measurement is volumetric analysis using centrifuging or filtering techniques; and then there are non-destructive techniques, such as using ultrasound or techniques based on using X-rays.

In the filter group of techniques, mention can be made in particular of the ALCAN method known under the name PODFA which is based on the following principles: about 2 kg of alloy are taken directly while in molten form. This alloy to be tested is caused to pass through a filter. The residue in the filter is then selected vertically along the central plane and prepared for metallographic analysis. The analysis makes it possible to determine the concentration of impurities or inclusions expressed in $mm^2/kg$. To cause the alloy to pass through the filter, it is necessary to apply air at sufficient pressure onto the free surface of the alloy in the receptacle which contains it.

However, it will be understood that that filter-based technique requires subsequent metallographic analysis, which takes a certain amount of time, and which therefore means that genuinely instantaneous analysis cannot be provided while the alloy is being made.

SUMMARY OF THE INVENTION

An object of the present invention is to provide a method and an apparatus for determining impurities in a metal alloy that enable such determination to be performed quickly and continuously while the alloy is being made.

To achieve this aim, the apparatus for determining the purity of a metal alloy is characterized in that it comprises:

- a shell defining a receptacle of generally tapering shape about a vertical axis having an open top end and a bottom end defining an orifice of small dimensions;
- a filter obstructing said orifice completely;
- means for initially raising said shell to a first predetermined temperature;
- means for placing a predetermined quantity of liquid alloy to be tested in said receptacle, said quantity of alloy initially being at a second predetermined temperature, whereby said alloy flows under gravity alone through said filter until the filter becomes clogged by the impurities contained in said alloy; and
- means for recovering and measuring the volume of alloy that has passed through said filter prior to it becoming clogged by the impurities contained in the alloy, whereby the purity of said alloy is deduced.

It will be understood that implementing the above apparatus is very simple since it suffices to take a sample from the alloy while it is being made, to put the sample in the receptacle closed by the filter, and to use any appropriate means for measuring the quantity of alloy that possess through the filter before it becomes clogged by the impurities, it being understood that the shell constituting the receptacle is maintained at a predetermined temperature.

In a preferred implementation of the invention, for an aluminum alloy, the filter is an extruded ceramic filter. Also preferably, the filter has porosity of about 300 cells per square inch (CSI).

Also preferably, the apparatus for determining the purity of the alloy is mounted on a moving carriage. The shell and a pan for recovering the alloy that has passed through the filter and for determining the quantity thereof are pivotally mounted relative to the chassis of the carriage about horizontal axes.

This makes the apparatus very easy to use.

The invention also provides a method of determining the purity of a metal alloy, characterized in that it comprises the following steps:

- a predetermined quantity of a liquid alloy to be tested is put into a tapering shell raised initially to a second predetermined temperature, said alloy being at a first predetermined temperature, said shell having a bottom provided with an orifice closed by a filter through which the alloy passes;
- the alloy is allowed to flow under gravity through said filter;
- the quantity of alloy that passes through said filter until the filter becomes clogged by the impurities in the alloy is collected; and
- the volume of the collected alloy is determined, from which the purity of said alloy is deduced.

BRIEF DESCRIPTION OF THE DRAWINGS

Other characteristics and advantages of the present invention appear more clearly on reading the following description of various embodiments of the invention given as non-limiting examples. The description refers to the accompanying drawings, in which:

FIG. 5 is a diagram illustrating the use of the FIG. 1 apparatus.

DESCRIPTION OF THE INVENTION

As already mentioned, the principle of the invention consists in placing a predetermined quantity of the alloy to be tested at a predetermined initial temperature in a shell of generally tapering shape about a vertical axis. The shell is maintained at a predetermined temperature and the alloy flows through a filter having characteristic details that are given below. The quantity of alloy that has passed through the filter is collected in a pan in order to determine the volume of alloy that passes through the filter before it becomes clogged by impurities, and naturally various techniques can be envisaged for measuring the quantity of alloy that has passed through the filter.

Figure 1:
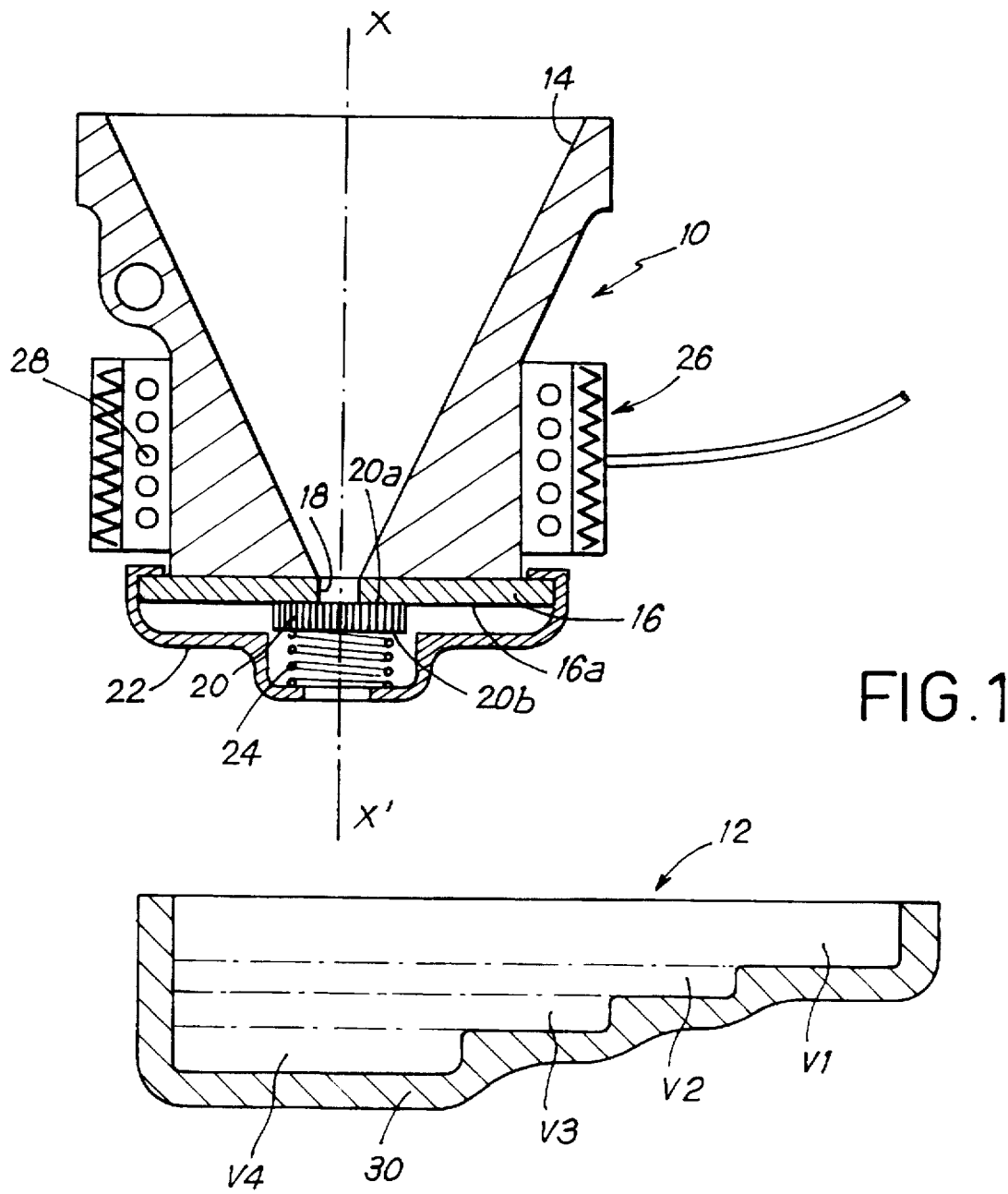
FIG. 1 is a detail view in vertical section showing both a filter shell and a pan for recovering alloy.

With reference initially to FIG. 1, details of a preferred embodiment of the apparatus for determining the purity of a metal alloy are described.

In the embodiment under consideration as shown in FIG. 1, the apparatus for determining the purity of an alloy essentially comprises a filter shell 10 and a pan 12 for recovering the filtered alloy. More precisely, the shell 10 defines a downwardly tapering receptacle 14 about a vertical axis XX'. The section of the receptacle 14 decreases going downwards. The bottom portion of the shell 10 is associated with a plate 16, preferably a removable plate, which defines an orifice of calibrated section 18 communicating with the bottom portion of the tapering receptacle 14. Beneath the orifice 18 there is removably fixed a filter 20 which is pressed in sealed manner against the bottom face 16a of the plate 16, e.g. by a clamp 22 and a spring system 24. Nevertheless, the filter 20 could be fixed differently to the bottom end of the shell 10, providing the filter 20 overlies the orifice 18 completely and providing it is fixed in sealed manner relative to the shell. In addition, the shell 10 has a temperature regulation system 26 which may be constituted, for example, by a heating resistor 28. The temperature regulation system 26 serves to maintain the shell at a constant predetermined temperature prior to any operation of determining alloy purity. The temperature of the shell is increased by the heat provided by the alloy. The top portion of the shell is open and is therefore at atmospheric pressure.

In the embodiment shown in FIG. 1, the purity-determining apparatus also includes a pan 12 located beneath the filter 20, with the pan 12 serving to collect all of the fraction of the alloy that passes through the filter 20 before the filter becomes clogged by the impurities contained in the alloy. In order to facilitate immediate determination of the volume that has passed through the filter, the bottom 30 of the pan 12 is stepped. Thus, for example, it can determine a bottom volume V4, a first intermediate volume V3, a second intermediate volume V2, and a top volume V1. It will be understood that the stepped bottom of the pan makes it possible to determine visually and easily an approximation to the volume and thus to the weight of alloy that has passed through the filter merely by observing which step of the stepped bottom is level with the free surface of the alloy in the pan 12. Naturally, the number of volumes defined by the pan could be different from that shown, and the number of steps could be different, with the pan thus giving various different approximations concerning the purity of the alloy.

Naturally, it is also possible to use other methods of determining the volume of alloy that has passed through the filter.

In a preferred embodiment corresponding aluminum alloys, and in particular to the alloy A-S7G, the filter 20 is an extruded ceramic filter having pores that are substantially perpendicular to the main faces 20a and 20b of the filter. Also preferably, the porosity of the filter expressed in CSI is about 300. CSI stands for the number of cells per square inch.

It would also be understood that the alloy flows through the filter merely under gravity. Preferably, the shell 10 is maintained by the regulation system 28 at a temperature lying in the range 450° C. to 350° C. and more preferably in the range 420° C. to 430° C. In addition, when the metal is put into the shell 10 the metal is maintained at a maximum temperature of 790° C. and a minimum temperature of 750° C. for the above-mentioned alloy. Also, in a preferred embodiment for aluminum alloys, the right cross-sectional area of the orifice 18 is equal to 1 cm$^3$. This value is not critical, but it will be understood that to ensure that the filter does indeed become clogged as a function of impurities contained in the alloy, it is necessary for the working section of the filter 20 to be small compared with the volume of alloy placed in the receptacle 14 as defined by the shell 10.

Figure 2:
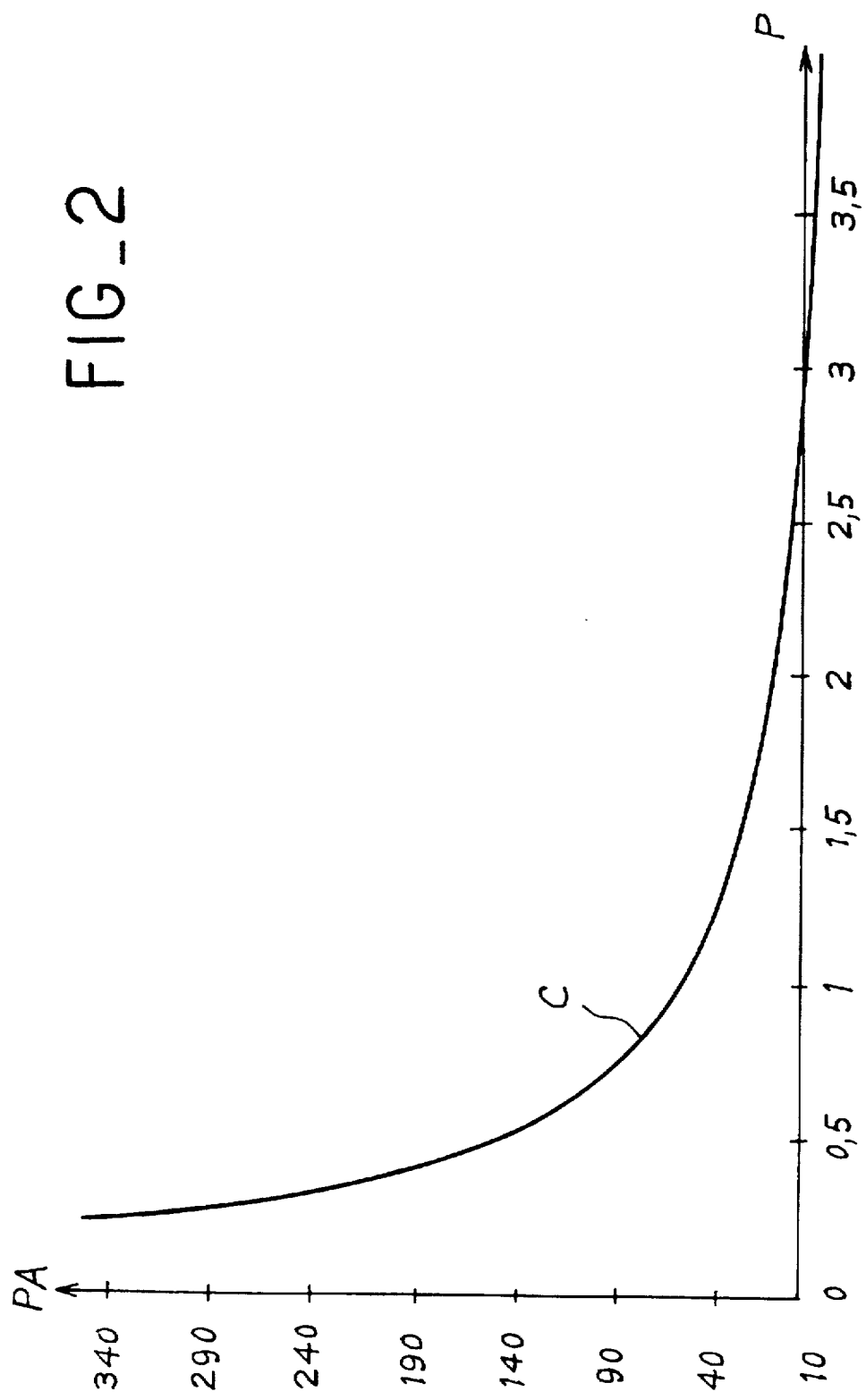
FIG. 2 is a graph showing a calibration curve for the purity of the alloy as a function of the quantity of alloy that has passed through the filter.

FIG. 2 is a graph of a calibration curve C making it possible to associate the weight P of alloy collected in the pan 12, i.e. the weight of alloy that has passed through the filter, with the alloy purity PA expressed in mm$^2$/kg for the A-S7G alloy. Using this curve, it is possible to associate the weight of alloy that has passed through the filter with a value for its purity. More precisely, it is possible to determine various zones of purity corresponding to criteria associated with different uses for the alloy. These zones correspond to the volumes defined by the steps in the pan of FIG. 1.

In the above detailed description, it is assumed that the apparatus is for determining the purity of an aluminum alloy. As already explained, it is with this type of alloy that determining purity is most critical because of the ease with which the metal is oxidized.

Nevertheless, the method and the apparatus of the invention can be applied to determining the purity of other alloys such as copper alloys, and cast iron. It is then necessary to match the above-described specific parameters to the particular requirements of the alloy. These parameters are the first and second temperatures and the structure and the porosity of the filter.

More generally, the shell must be maintained, prior to testing, at a temperature lying in the range 100° C. to 500° C. and depending on the nature of the alloy. The initial temperature of the alloy to be tested must lie in the range $T_l+50°$ C. to $T_l+250°$ C., where $T_l$ is the liquidus temperature of the alloy. Depending on the alloy to be tested, this temperature will lie in the range 650° C. to 850° C.

The nature of the filter must match the temperature involved. For example, with cast iron, the filter must be made of a material that is more refractory.

Figure 3:
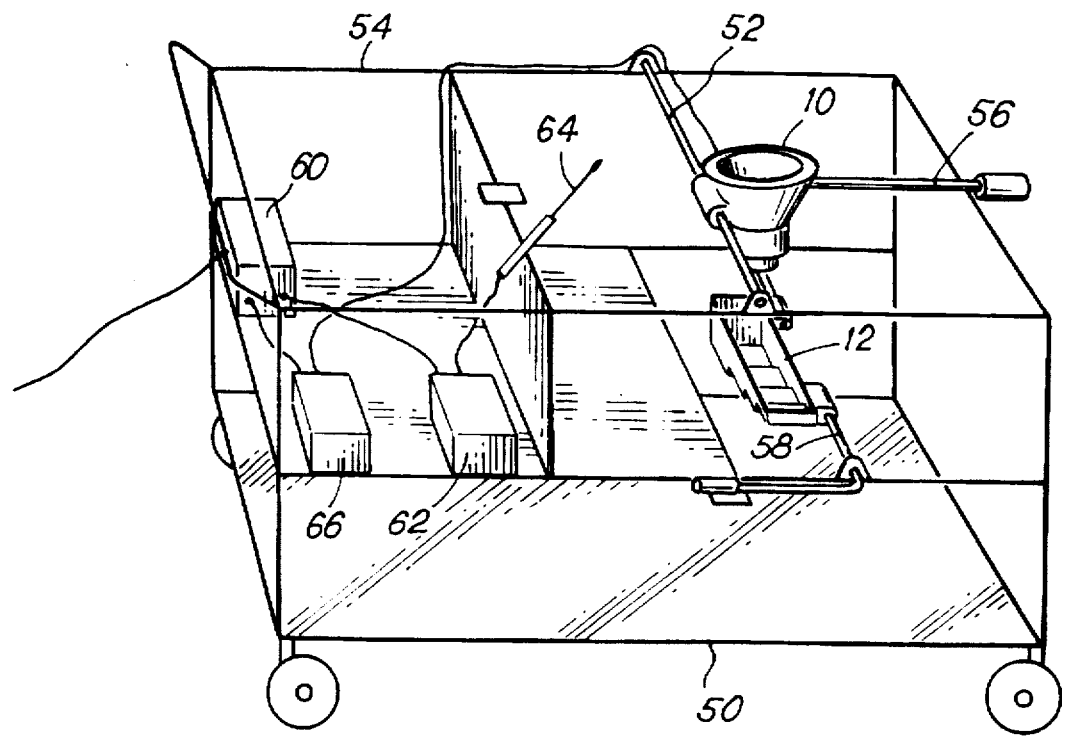
FIG. 3 shows a preferred embodiment of the apparatus for determining the purity of an alloy mounted on a moving carriage.
Figure 4:
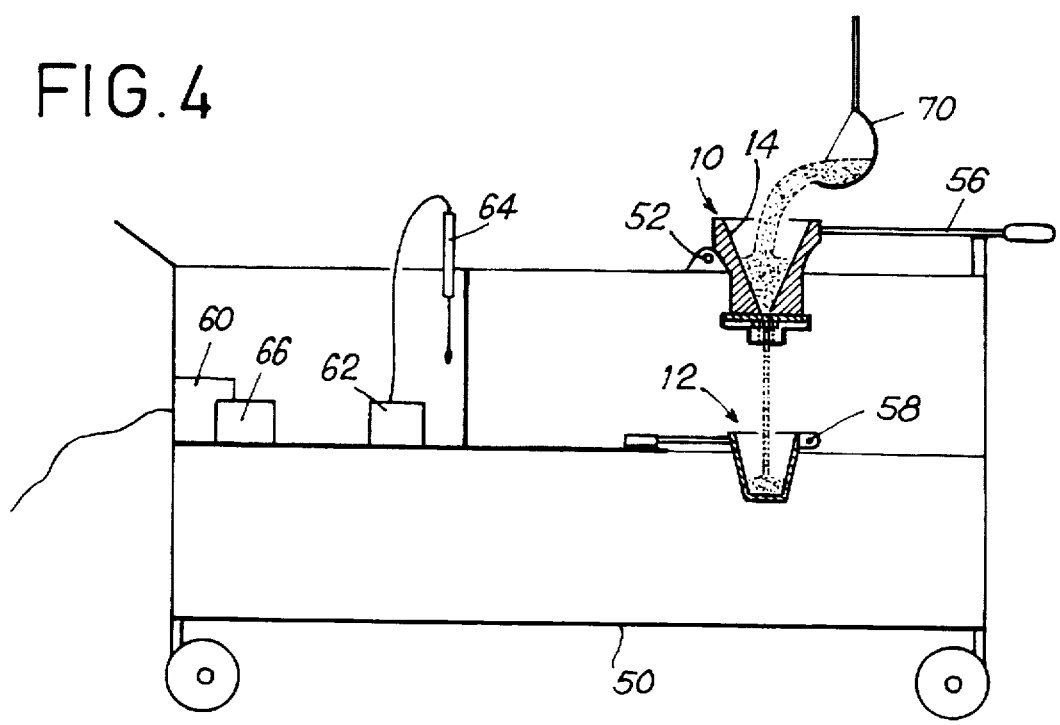
FIG. 4 shows an intermediate step in the use of the FIG. 3 apparatus.

With reference now to FIGS. 3 and 4, there follows a description of a complete preferred embodiment of apparatus for determining the purity of an alloy. The apparatus comprise a moving carriage 50 on which there are mounted, one above the other, the shell 10 and the pan 12. The shell 10 is preferably pivotally mounted about a horizontal axis 52 connected to the chassis 54 of the carriage 50, and a handle 56 makes it possible to move the shell 10 from its in-use position with a vertical axis to an upside-down position enabling the alloy residue to be removed at the end of a test operation. Similarly, and preferably, the pan 12 is pivotally mounted about a horizontal axis 58, thereby enabling the pan 12 to be emptied by being tipped over once the test has been completed. The carriage 50 also carries an electricity power supply 60 which powers both a digital display 62 and a temperature probe 64 for measuring the temperature of the alloy when it is put into the shell 10. In addition, the temperature regulation system 66 is designed to regulate the temperature of the shell 10 by means of the heating collar 28. It will be understood that the moving carriage 50 thus includes all of the elements required for performing a test on alloy purity.

In FIG. 4, there is shown an intermediate step in the test operation. The shell 10 and the pan 12 are in the in-use positions, i.e. their axes are vertical, and a ladle 70 is shown from which a desired-volume sample of liquid alloy for testing has been taken, the ladle 70 serving to pour the alloy into the tapering receptacle 14 of the shell 10 as it drains away. Before it is poured, the alloy contained in the ladle 70 has its temperature measured by means of the temperature probe 64.

To enable the apparatus to be used with any aluminum alloy end over a wide range of temperatures, the apparatus can be used with two different dimensions of filter section being defined by the orifice 18. Section can be changed by changing the plate 16 situated beneath the shell 10, with each plate having an orifice of appropriate section.

The charge of FIG. 5 gives temperature ranges for various aluminum alloys, each comprising two filter sections enabling purity measurements to be performed with suitable sensitivity.

The small filter section is 1 cm$^2$.

The large filter section is 2 cm$^2$.

All of the temperatures given in the chart of FIG. 5 should be increased by 20° C. for alloys that have been modified with sodium. Sodium greatly increases the viscosity of such alloys. It is therefore essential to raise its temperature in order to achieve the same sensitivity for the apparatus.

To calibrate the apparatus for determining the purity of an alloy, the founder initially performs a reference measurement using a bath whose state of oxidation does not require it to be rejected because of the presence of too much oxide. Thereafter, routine measurements on the same alloy made at the same temperature make it possible to compare the number of steps filled in the pan with the number filled during the reference measurement.

It can thus be seen that the determination apparatus shown in FIG. 3 is particularly advantageous since it is entirely self-contained, including the pan and the shell, together with all of the monitoring elements and temperature regulation elements. Furthermore, because it is movable, the entire apparatus can be brought close to a melting furnace, to a furnace for maintaining the liquid state, or to a transfer vessel containing the alloy. Also, because the pan and the shell are mounted to pivot about horizontal axes, these two receptacles are easily emptied after tests have been performed.

Finally, it will be understood that the particular mounting for the filter 20 on the bottom portion of the shell as shown in FIG. 1 makes it easy to replace it with a new filter after each test operation.

It should be emphasized that it is directly the liquid alloy coming from the alloy-making furnace that is poured into the shell. It will be understood that the heater means associated with the shell serve solely to regulate the initial temperature thereof and under no circumstances to melt the alloy which is poured into the shell in liquid form and at a desired temperature.

We claim:

1. Apparatus for determining the purity of a metal alloy comprising:

a shell defining a receptacle of generally tapering shape about a vertical axis having an open top end and a bottom end defining an orifice of small dimensions;

a filter obstructing said orifice completely;

means for initially raising said shell to a first predetermined temperature prior to the alloy being inserted therein;

means for placing a predetermined quantity of liquid alloy to be tested in said receptacle, said quantity of alloy initially being at a second predetermined temperature higher than the first predetermined temperature, wherein said alloy flows under gravity alone through said filter until the filter becomes clogged by the impurities contained in said alloy; and means for recovering and measuring the volume of alloy that has passed through said filter prior to it becoming clogged by the impurities contained in the alloy, wherein the purity of said alloy is deduced from said volume that has passed through the filter.

2. Apparatus according to claim 1, wherein said filter is an extruded ceramic filter, said alloy being an aluminum alloy.

3. Apparatus according to claim 2, wherein said filter has a porosity of about 300 cells per square inch (CSI), said alloy being an aluminum alloy.

4. Apparatus according to claim 3, wherein said orifice has a right cross section area of 1 or 2 cm$^2$.

5. Apparatus according to claim 4, wherein the first predetermined temperature is 350–450° C.

6. Apparatus according to claim 2, wherein said second predetermined temperature lies in the range 650° C. to 850° C.

7. Apparatus according to claim 2, wherein said first predetermined temperature lies in the range 450° C. to 350° C.

8. Apparatus according to claim 1, wherein said orifice of the shell has a right cross-section of area that is of the order of 1 cm$^2$ or 2 cm$^2$.

9. Apparatus according to claim 1, wherein said second predetermined temperature lies in the range $T_l+50°$ C. to $T_l+250°$ C., $T_l$ being the liquidus temperature of the alloy.

10. Apparatus according to claim 1 wherein the means for recovering and measuring the volume of alloy comprise a pan disposed beneath the filter, said pan having a stepped bottom, each step of the stepped bottom corresponding to a degree of purity of said alloy.

11. Apparatus according to claim 10, having a moving carriage and wherein in that said shell is mounted on said carriage to pivot about a horizontal axis, in that said pan is mounted on said carriage to pivot about a horizontal axis, and in that said carriage also includes means for monitoring the temperature of said alloy before it is poured into said shell, heater means surrounding said shell, and means for regulating said heater means.

12. A method of determining the purity of a metal alloy comprising the steps of:

providing a predetermined quantity of a liquid alloy to be tested in a tapering shell, said alloy being at a second predetermined temperature, said shell having a bottom provided with an orifice closed by a filter prior to the alloy being provided, and through which the alloy passes;

allowing the alloy to flow under gravity alone through said filter while said shell is maintained at a first predetermined temperature lower than the second predetermined temperature;

collecting the quantity of alloy that passes through said filter until the filter becomes clogged by the impurities in the alloy; and determining the volume of collected alloy, from which the purity of said alloy is deduced.

13. A method according to claim 12, wherein said second predetermined temperature lies in the range 650° C. to 850° C., and said first predetermined temperature lies in the range 450° C. to 350° C., said alloy being an aluminum alloy.

14. A method according to claim 12, wherein said filter is an extruded ceramic filter, said alloy being an aluminum alloy.

* * * * *